United States Patent [19]

Hokse et al.

[11] Patent Number: 4,477,568

[45] Date of Patent: Oct. 16, 1984

[54] PROCESS FOR THE MANUFACTURE OF CYCLODEXTRIN

[75] Inventors: Hendrik Hokse, Tynaarlo; Frederik S. Kaper, Blijham; Jacob T. Wijpkema, Siddeburen, all of Netherlands

[73] Assignee: Proefstation voor Aardappelverwerking-TNO en Cooperatieve Verkoop en Produktievereniging van Aardappelmeel en Derivaten AVERE B.A., Groningen, Netherlands

[21] Appl. No.: 419,800

[22] Filed: Sep. 20, 1982

[30] Foreign Application Priority Data

Sep. 24, 1981 [NL] Netherlands ......................... 8104410

[51] Int. Cl.$^3$ ......................... C12P 19/18; C12N 9/18
[52] U.S. Cl. ..................................... 435/97; 435/197; 435/803; 435/813
[58] Field of Search ................. 435/97, 193, 803, 813, 435/178, 188

[56] References Cited

U.S. PATENT DOCUMENTS

| 2,642,376 | 6/1953 | Gale et al. | 435/188 |
|---|---|---|---|
| 3,812,011 | 5/1974 | Okada et al. | 435/97 |
| 3,923,598 | 12/1975 | Horikoshi | 435/97 |
| 3,988,206 | 10/1976 | Shiosaka et al. | 435/193 |
| 4,135,977 | 1/1979 | Horikoshi et al. | 435/97 |
| 4,317,880 | 3/1982 | Heady | 435/94 |
| 4,317,881 | 3/1982 | Yagi et al. | 435/97 |

FOREIGN PATENT DOCUMENTS

| 2482620 | 11/1981 | France | 435/193 |
|---|---|---|---|
| 56-124382 | 10/1981 | Japan | 435/193 |

OTHER PUBLICATIONS

French et al., in Die Starke No. 8 (1963) pp. 280-284.
Nakamura et al., in Agr. Biol. Chem. vol. 40 (9), 1785-1791 (1976).
Hokse in Journal of Chromatography vol. 189 (1980) pp. 98-100.

Primary Examiner—Lionel M. Shapiro
Attorney, Agent, or Firm—Daniel J. Reardon

[57] ABSTRACT

A process for producing cyclodextrin from starch in which an aqueous solution of starch is subjected to the action of an active cyclodextrin glycosyltransferase and the reaction mixture containing cyclodextrin, starch degradation products and active enzyme is continuously subjected to an ultrafiltration process to effect passage of the formed cyclodextrin through the membrane, while retaining substantially all of the other starch degradation products and active enzyme, thus permitting more cyclodextrin to be formed in the retentate, which will then pass the membrane, collecting the aqueous solution of cyclodextrin and recovering the cyclodextrin.

4 Claims, 1 Drawing Figure

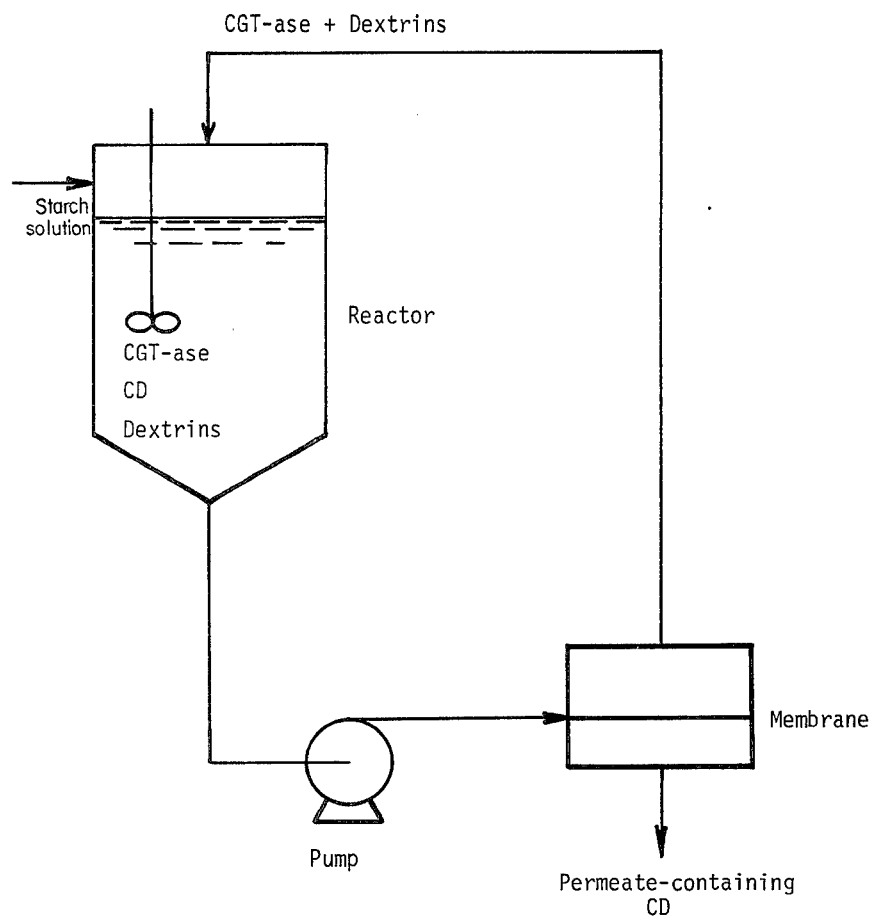

PROCESS FOR THE MANUFACTURE OF CYCLODEXTRIN

The invention relates to a process for the manufacture of cyclodextrin by enzymatic conversion of amylaceous raw materials.

Cyclodextrins are cyrstalline, cyclic oligosaccharides, which usually consist of 6, 7, or 8 α-D-glucopyranose units (called α-, β-, or γ-cyclodextrin, respectively), linked to each other by 1-4 bonds. The three cyclodextrins mentioned differ from each other with respect to solubility in water, optical rotation, crystal form, etc.

It was Schardinger who discovered that *Bacillus macerans* can form an enzyme, which produces cyclodextrins from starch. With this enzyme from *Bacillus macerans* a mixture of cyclodextrins is being obtained in rather low yield. The mixture has to be fractioned by the addition of toxic organic solvents, such as trichloroethylene or bromobenzene. The use of such precipitants is complicated and expensive and makes the cyclodextrins unsuitable for food purposes. Later on, other microorganisms have been discovered which produce a cyclodextrin forming enzyme, cyclodextrin glycosyltransferase (EC 2.4.1.19) which often is abbreviated to CGT-ase. As such can be mentioned:

| Bacillus megaterium T 5 | (ATCC 21737) | U.S. PAT. 3,812,011 |
|---|---|---|
| Bacillus stearothermophilus | (FERM-P 2217) | U.S. PAT. 3,988,206 |
| Bacillus Sp. 38-2 | (ATCC 21783) | U.S. PAT. 3,923,598 |
| Bacillus Sp. 135 | (ATCC 21595) | " |
| Bacillus Sp. 169 | (ATCC 21594) | " |
| Bacillus Sp. 13 | (ATCC 31006) | " |
| Bacillus Sp. 17-1 | (ATCC 31007) | " |
| Micrococcus Sp. | Eur. patent appl. 0.017.242. | |

Some of these CGT-ases have the advantage that they form relatively large amounts of β-cyclodextrin, which makes the isolation of crystalline β-CD from the mixture which further contains α-CD, γ-CD and acyclic dextrins somewhat easier.

None the less for a process on an industrial scale, where for economical reasons relatively high starch concentrations need to be used, the isolation of pure β-CD from the outer cyclodextrins and dextrins is quite laborious, the net result being that in the production of crystalline β-CD a huge amount of mother liquor containing α-CD, γ-CD and other glucose polymers is obtained.

U.S. Pat. No. 4,135,977 describes a method for improving the yield of crystalline β-CD in which the glucoamylase is added to the reaction mixture formed by CGT-ase from starch. In this way the starch degradation products which were not converted to CD are broken down to glucose, maltose and oligosaccharides. The digest is then decolorised, demineralised and concentrated, whereupon a small amount of β-CD is added as a seed. In this way crystalline β-cyclodextrin is obtained, but the amount of mother liquor (containing α-, β-, γ CDs, glucose, maltose and oligosaccharides) is about 4 or 5 times that of β-CD. Therefore, a definite need exists for a process by which more cyclodextrin and less byproducts are being produced by the reaction of CGT-ases on starch.

An object of this invention is to provide an improved process for producing high amounts of cyclodextrin by reacting starch with a cyclodextrin glycosyltransferase, taking care that a minimum amount of acyclic byproducts is being formed.

Another object of this invention is to provide a novel process in which cyclodextrin is recovered in a high yield and easily from the mixture formed by the enzymatic reaction of cyclodextrin glycosyltransferase on starch.

A further object of this invention is to provide a novel process in which β-cyclodextrin is recovered in high yields and easily from the reaction of specific cyclodextrin glycosyltransferases on starch.

These and other objects can be obtained according to the invention by performing the reaction between starch and CGT-ase in such a way that the aqueous reaction mixture of CGT-ase and starch is subjected to an ultrafiltration process whereby substantially all the formed cyclodextrins will pass the membrane, while the enzyme and the residual starch degradation products are being retained, this causing additional formation of cyclodextrin which will pass through the membrane, thereby leaving a minimum of starch degradation products as a byproduct of the reaction.

Our invention therefore comprises a process for producing cyclodextrin from starch in which an aqueous solution of starch is subjected to the action of an active cyclodextrin glycosyltransferase and the reaction mixture containing cyclodextrin, starch degradation products and active enzyme is continuously subjected to an ultrafiltration process to effect passage of at least a substantial portion of the cyclodextrin through the membrane, while retaining substantially all of the other starch degradation products and active enzyme, thus permitting more cyclodextrin to be formed in the retentate which will then pass the membrane, collecting the aqueous solution of cyclodextrin and recovering the cyclodextrin.

In order to obtain high yields of β-cyclodextrin an enzyme which has a high activity to form specifically β-CD, which will be described later on, is being used.

If starch is used at a low concentration, in the order of 1% (w/v) fairly high yields of CD can be obtained in a solid wall reactor. Such low operating concentrations require a large volume of reaction vessel and a lot of water must be evaporated in the concentration step preceding the isolation of CD. As starch is a cheap raw material, the use of high starch concentrations would have significant economic advantages for production of CD on an industrial scale.

Unfortunately the yield of CD based on starch in a solid wall reactor declines considerably at higher concentrations due to an incomplete conversion of starch into CD. When according to the invention the mixture of partially degraded starch and CD is subjected under a pressure gradient to an ultrafiltration membrane with a distinct molecular weight cutoff the CD will preferentially be removed from the equilibrium mixture, thus enabling additional formation in the retentate of CD from partially converted starch degradation products, thus enhancing the yield to economically and technologically attractive levels.

The feasability of the CD separation can be demonstrated using a laboratory membrane reactor, such as an Amicon-Model 202. The reaction and separation may be performed batchwise, but it is preferred to feed continuously a mixture of CGT-ase and starch solution in the cell. Due to the low membrane area to volume ratio these ultrafiltration cells have limited commercial value.

For a commercial process the ratio of membrane surface to volume will have to be maximized. For this reason we prefer in this case a continuous, reactive flow system (see FIG. 1) in which the enzyme flows with the substrate past membrane walls. From the large scale commercial ultrafiltration units we prefer to make use of those consisting of tubular membranes. This type of ultrafiltration membranes has the advantage that owing to the flow conditions the least possible concentration polarization of unreacted starch and starch degradation products (acyclic dextrins) occurs. Moreover, tubular membranes can be more easily cleaned than other types of membranes, such as plate and frame type or hollow fibre type membranes.

The pressure gradient should be in the order of 10–50 p.s.i. and preferably be at least 15 p.s.i. The porosity of the membrane should be such that cyclodextrins will easily pass, whereas the acyclic dextrins should substantially be retained. For this reason we preferably use membranes with a molecular weight cutoff in the order of 5000–10000, e.g. Amicon YM 5, Amicon PM 10 or DDS 800 membranes.

In a typical commercial process for producing CD from starch we generally would start with a sustrate with a dry solids content of at least 10% by weight and preferably a dry solids content of between 15 and 30% by weight.

Solubilization of starch in water can be conveniently accomplished by the use of high temperature jetcookers, e.g. operating at temperatures of 140° C. or higher and at pressures above atmospheric. In some instances a starch thinning enzyme such as alpha-amylase, can be used in order to reduce the viscosity of the starch solution, thereby maintaining the DE (dextrose equivalent) lower than 10.

Suitable starch raw materials are starches from corn, waxy maize, wheat, sorghum, potatoes, tapioca, sago and rice. Also soluble starch and separated starch fractions (i.e. amylopectin) can be used.

The present invention is particularly adaptable to the production of crystalline β-cyclodextrin from amylaceous materials. In this case a CGT-ase is needed which preferentially forms β-CD in comparison with α-CD and γ-CD.

We have found that the microorganisms *Bacillus circulans* RIV nr.11115 can form a CGT-ase which actively forms cyclodextrins in high yield, in particular β-cyclodextrin.

This microorganism was isolated by maintaining flax retting water from Zealand Flanders at temperatures of 37° C. resp. 48° C. and taking samples at will and after pasteurisation at 80° C. plating those out on the following medium:
Soluble starch: 20 g/l
Peptone: 5 g/l
Yeast extract: 5 g/l
$K_2HPO_4$: 1 g/l
$MgSO_4 7H_2O$: 0.2 g/l
$FeCl_3.6H_2O$; 20 mg/l
Agar: 18 g/l
The pH was fixed with $Na_2CO_3$ at 8.5.

The plates were incubated at 37° C. and 48° C. during 96 hours at maximum. Isolated colonies were inoculated on fresh plates and incubated once more under the same conditions.

To detect the formation of CGT-ase the microorganisms were inoculated on shaked cultures and after the growth period the cells were separated by centrifugation and a sample of the supernatant was added to a 1% amylopectin solution.

The composition of the carbohydrates so formed was determined by liquid chromatography. Pure cultures of the CGT-ase forming microorganisms were made in slanted tubes. In this way a microorganism 251 was isolated, which was determined by the RIV at Bilthoven the Netherlands as *Bacillus circulans* mannitol-negative, RIV nr. 11115. This culture is deposited at the Laboratory of Microbiology at Delft under number LMD 81103.

The determination gave the following results:
Morphology: Spores oval, subterminal-terminal, distinctly protruding.
Acid formation from carbohydrates: at 37° C., aerobic, not enriched acid formation from glycerol, arabinose, xylose, glucose, mannose, salicine, maltose, lactose and sucrose; no acid formation from aldonitol, rhamnose, dulcitol, inositol, mannitol, sorbitol and gluconate
Growth: good aerobic anaerobic growth at 42° C. (also in 5% NaCl), no growth in 6.5% NaCl
Various conversions: no gas from glucose strongly oxidase positive catalase positive indol negative $H_2S$ formation negative urea negative nitrate reduction negative, no gas from nitrate gelatinase positive acetoin negative The fermentation of *Bacillus circulans* RIV nr. 11115 is done in the following way:
Soluble starch: 12.5 g/l
Pepton: 5 g/l
yeast extract: 5 g/l
$K_2HPO_4$: 1 g/l
$KH_2PO_4$: 1.5 g/l
$MgSO_4.7H_2O$: 0.2 mg/l
$FeCl_3.6H_2O$: 20 mg/l
pH at the start: 6.9
pH regulation: 5.0 pH 7.0 with titrator 2N NaOH and 2N $H_2SO_4$
Sterilisation: simultaneous in fermentor, 30 min. 120° C.
Temperature: 48° C.
Fermentation time: 10–15 hours
Aeration: 1 l/min./l medium at 400–800 rpm agitation velocity
Antifoam: 1 $cm^3$ MS-10 per liter; additional supply of suspension of MS 10 in 0.2% xanthan gum (MS=Midland Silicones)
Inoculation: 5–10% from earlier fermentation batch
Sampling: automatically every 2 hours
Determination total carbon: Beckman Model 915B TOC-Analyzer.
Determination cell growth: Optical density at 650 nm. Turbidity determination after 5x dilution.
Determination acetic acid: gaschromatographic analysis.

Typical features are:
1° The fermentation temperature of 48° C.; at this temperature growth and CGT-ase formation is far better than at 37° C.
2° The relatively short fermentation time.
3° The fact that enzyme formation is linked to the growth.

The enzyme can be recovered from the fermentation broth in a traditional way, such as:

(a) clarification of the broth and concentrating by evaporation
(b) salting out e.g. with ammonium sulfate
(c) precipitation with organic solvents such as ethanol
(d) adsorption on DEAE-cellulose, cross-linked dextran or starch followed by elution.

An attractive method, which is preferably used, consists of adsorption of the enzyme on special starch products after clarification and, if desired, concentration through ultrafiltration of the broth. The special starch products are of such type, that they are insoluble in water at room temperature, but are soluble in water at 50°-65° C. As a result of this property, the complex of enzyme and starch product can be used as such for making cyclodextrin, no desorption being needed. This type of starch products is obtained by dissolving starch, amylopectin or amylose completely in water, retrograding the starch product by the action of time, salts and/or freezing temperatures and isolating the precipitated starch products—if needed after thawing—and drying them. Such retrograded starch products have a greater adsorption capacity for CGT-ase than native starch or heated moist starch. Since they dissolve almost completely in water at 50°-65° C. elution of the enzyme becomes superfluous. The starch products can be added to the fermentation broth in amounts of 1 g to 5 g/l, preferably max. 3 g/l. Addition of ammonium sulfate or organic solvents is not necessary. It suffices to stir for 30-45 minutes, to filter off the starchenzyme complex, to wash it with cold water and to dry.

The pH optimum of the enzyme complex was determined as follows:

Substrate: 1% soluble starch in buffer
Enzyme-substrate ratio: 10 mg-5 ml substrate solution
Temperature: 35° C.
Reaction time: 4 hours
Buffers: pH 4-6 0.01 M citrate
: pH 6-7.5 0.01 M phosphate
: pH 7.5-9 0.01 M tris
Analysis: liquid chromatography as described in Journal of Chromatography 189 (1980) p. 98-100.
In this way one pH optimum was found at pH 6-6.5, which clearly differs from the pH optimum of the CGT-ases mentioned in U.S. Pat. No. 3,923,598.

The temperature stability was measured as follows:
pH: 6 (0.01 M Calcium acetate)
Substrate: 10% soluble starch in buffer
Enzyme/substrate ratio: 10,25 and 50 mg enzyme- 5 and 10 ml substrate solution
Reaction time: up to 44 hours
Temperature: 35°, 50°, 55°, 60° and 65° C.
Analysis: liquid chromatography, dilution 1:8 with water These tests showed that the enzyme is stable at 60° C., but that the activity of the enzyme declines considerably at 65° C.

The Influence of Calcium on Enzyme Stability

Temperature: 65° C.
pH: 6
Substrate: 10% soluble starch in buffer
Reaction time: up to 44 hours
Analysis: as above
Buffer: 0.01 m Na-citrate with resp. 0.1 and 10 m.mol. Ca-acetate per liter
Enzyme/substrate ratio: 25 mg.-10 ml. substrate solution These tests show that the presence of calcium has a stabilising action on the enzyme.

Production of β-CD

Temperature: 60° C. for 5 and 10% starch concentration 50° C. for 1 and 2% starch concentration
pH: 6
Substrate: soluble starch, resp. 10, 5, 2 and 1%
Reaction time: 44 hours
Enzyme-substrate ratio: max. 50 mg., min 5 mg. enzyme per 5 ml. substrate solution
Analysis: as above The results are listed in the following table:

TABLE A

Production of CD at various starch concentrations. Composition of reaction mixture after 44 hours reaction:

| | % conc. soluble starch | Enz. prep. mg. | % rest polymer | % α-CD | % β-CD | % γ-CD | % CD | α:β:γ |
|---|---|---|---|---|---|---|---|---|
| 1 | 10 | 10 | 86.6 | 1.2 | 9.9 | 2.3 | 13.4 | 1:8.3:1.9 |
| 2 | 10 | 25 | 77.7 | 2.5 | 15.7 | 4.1 | 22.3 | 1:6.3:1.6 |
| 3 | 10 | 50 | 70.1 | 2.8 | 20.4 | 6.7 | 29.9 | 1:7.3:2.4 |
| 4 | 5 | 5 | 87.6 | 1.5 | 9.1 | 1.8 | 12.4 | 1:6.1:1.2 |
| 5 | 5 | 10 | 73.2 | 2.8 | 18.9 | 5.1 | 26.8 | 1:6.8:1.8 |
| 6 | 5 | 25 | 65.5 | 3.9 | 25.1 | 5.5 | 34.5 | 1:6.4:1.4 |
| 7 | 2 | 5 | 67.7 | 3.3 | 22.8 | 6.2 | 32.3 | 1:6.9:1.9 |
| 8 | 2 | 10 | 61.9 | 4.3 | 27.9 | 5.9 | 38.1 | 1:6.5:1.4 |
| 9 | 2 | 15 | 52.1 | 6.0 | 33.5 | 8.4 | 47.9 | 1:5.6:1.4 |
| 10 | 1 | 5 | 54.0 | 6.0 | 35.0 | 5.0 | 46.0 | 1:5.8:0.8 |
| 11 | 1 | 10 | 40.0 | 8.0 | 40.0 | 12.0 | 60.0 | 1:5:1.5 |
| 12 | 1 | 15 | 39.5 | 8.0 | 40.0 | 12.5 | 60.5 | 1:5:1.6 |

This table shows that the new CGT-ase can produce in a solid wall reactor at least 60% CD, 66% of which consists of β-CD.

We preferably use 1-2% enzyme (g/g dry solids). Although the pH may vary from 4-7, we prefer to work at pH 5.5-6.5, whereas the reaction temperature is being kept below 65° C., preferably at 55°-60° C. The starch concentration is kept for commercial applications at 5%-30%, the reaction preferably being performed in combination with an ultrafiltration step. After the reaction the enzyme is inactivated by heating to 100°-120° C. After decolorisation and demineralisation the CD containing liquid is concentrated. The β-CD can be crystallised by lowering the temperature gradually to about 15° C. and seeding with a small amount of β-CD crystals. The crystalline β-CD can be separated by means of centrifuging and washed with a small amount of water.

If needed, it may be recrystallised in hot water. The mother liquor, which mainly contains α-, β-, and γ-cyclodextrin may also be used as a source of CD for various applications in practice.

It is also possible to concentrate the CD containing liquid without crystallisation of the β-CD to a solids content of about 70–80% and sell it in the form of a syrup. Another possibility is to spray dry the CD containing liquid and bring it on the market as a powder with at least 95% d.s.

An elegant method to fractionate the α-, β- and γ-CD in the CD containing liquid is by means of liquid chromatography on a porous polystyrene resin containing sulfonic acid groups preferably in the form of the calcium salt, such as Dowex 50 W-X2, Dowex 50 W-X4, Aminex AG 50 W-X4. Elution can be performed with warm water, rather than with organic solvents. α-CD is retained less strongly than γ-CD, whereas β-CD is retained stronger than γ-CD. The order of elution therefore is: α-CD, γ-CD, β-CD.

Cyclodextrins are very suitable for applications in practice, because they are able to form inclusion compounds with many chemical compounds. In this way volatile materials may be stabilised, materials sensitive to oxidation or UV degradation may be protected and various physical of chemical properties may be modified.

EXAMPLE I

A slurry of potato starch in tap water is passed through a jetcooker at a temperature of 150° C. The resulting aqueous starch solution has about 20% solids; the pH is adjusted to 6.5. This solution at a temperature of 60° C. is transferred to a membrane reactor (Amicon, Model 202) with YM 5 type membranes (molecular weight cutoff 5000) and converted with 0.01 g/g dry starch CGT-ase isolated from *Bacillus circulans* RIV nr.11115 adsorbed on retrograded amylopectin. The pressure gradient is kept at 10 p.s.i. and the volume in the membrane reactor is kept constant. The reaction is performed during 48 hours. Based on the starch raw material supplied into the reactor, the permeate contains 58.5% cyclodextrins, from which 42% crystalline β-CD (based on starch) could be recovered. In a solid wall reactor the yield of CD on starch at a 20% starch concentration is in the order of 18.5% out of which only 10% crystalline β-CD can be recovered.

EXAMPLE II

A 8.6% aqueous starch solution having a pH of 7.9 is converted during 6 hours at a temperature of 55° C. in the membrane reactor of Example I with 0.025 g. CGT-ase from Bac. sp. ATCC 21783 per 100 g. dry starch.

The UF permeate contains 60% CD (based on d.s.) from which 39.5% crystalline β-CD is recovered.

In a solid wall reactor the maximum amount of CD under the same conditions is in the order of 27%, from which 19.6% β-CD can be crystallised.

EXAMPLE III

The process of Example I is repeated during 5.5 hours at a pH of 5.5 and a temperature of 55° C. with a 8.8% aqueous starch solution containing per 100 g. dry starch 0.015 CGT-ase from *Bac. macerans*.

The UF permeate contains based on d.s. 68.4% of CD.

The maximum CD concentration which is being obtained in a solid wall reactor at the same starch concentration, pH and temperature is 31.6% based on d.s.

We claim:

1. A process for producing cyclodextrin from starch in which an aqueous solution comprising starch is subjected to the action of the active enzyme, cyclodextrin glycosyltransferase obtained by cultivation of *Bacillus circulans* RIV nr.11115, and the resulting reaction product comprising cyclodextrin, starch degradation products and the active enzyme is subjected to an ultrafiltration process to effect passage of the formed cyclodextrin through the membrane employed in said process, while retaining substantially all of the other starch degradation products and active enzyme, thus permitting more cyclodextrin to be formed in the retentate, which will then pass said membrane; and collecting the aqueous solution including said cyclodextrin.

2. A process according to claim 1, wherein said ultrafiltration process is continuous.

3. A process according to claim 2 in which the active cyclodextrin glycosyltransferase is adsorbed on a starch product which is insoluble in water of room temperature, but soluble in water of a temperature of 50°–65° C.

4. A process according to claim 2 wherein said cyclodextrin is β-cyclodextrin.

* * * * *